United States Patent
Bolduc et al.

(10) Patent No.: US 6,929,661 B2
(45) Date of Patent: Aug. 16, 2005

(54) MULTI-LUMEN PROSTHESIS SYSTEMS AND METHODS

(75) Inventors: Lee Bolduc, Sunnyvale, CA (US); Andrew L. Chiang, Fremont, CA (US)

(73) Assignee: Aptus Endosystems, Inc., Sunnyvale, CA (US)

(*) Notice: Subject to any disclaimer, the term of this patent is extended or adjusted under 35 U.S.C. 154(b) by 0 days.

(21) Appl. No.: 10/693,255

(22) Filed: Oct. 24, 2003

(65) Prior Publication Data

US 2005/0021132 A1 Jan. 27, 2005
US 2005/0113906 A9 Jan. 27, 2005

Related U.S. Application Data

(63) Continuation-in-part of application No. 10/271,334, filed on Oct. 15, 2002.
(60) Provisional application No. 60/489,011, filed on Jul. 21, 2003, and provisional application No. 60/333,937, filed on Nov. 28, 2001.

(51) Int. Cl.$^7$ .................................................. A61F 2/06
(52) U.S. Cl. ..................................... 623/1.35; 623/1.15
(58) Field of Search .............................. 623/1.11–1.16, 623/1.35, 1.36, 1.27, 1.5, 1.51, 1.53

(56) References Cited

U.S. PATENT DOCUMENTS 5,639,278 A * 6/1997 Dereume et al. .......... 623/1.13
6,576,009 B2 * 6/2003 Ryan et al. ................. 623/1.35

* cited by examiner

*Primary Examiner*—(Jackie) Tan-Uyen T. Ho
(74) *Attorney, Agent, or Firm*—Ryan Kromholz & Manion, S.C.

(57) ABSTRACT

Systems and methods introduce and deploy a multi-lumen prosthesis into a blood vessel or hollow body organ. The prosthesis has a trunk divided by an internal septum, which defines, within at least a portion of the trunk interior, a multi-lumen flow channel configuration. A lumen extension component can be sized and configured to be fitted within at least one of the interior lumens to define an extended lumen.

19 Claims, 7 Drawing Sheets

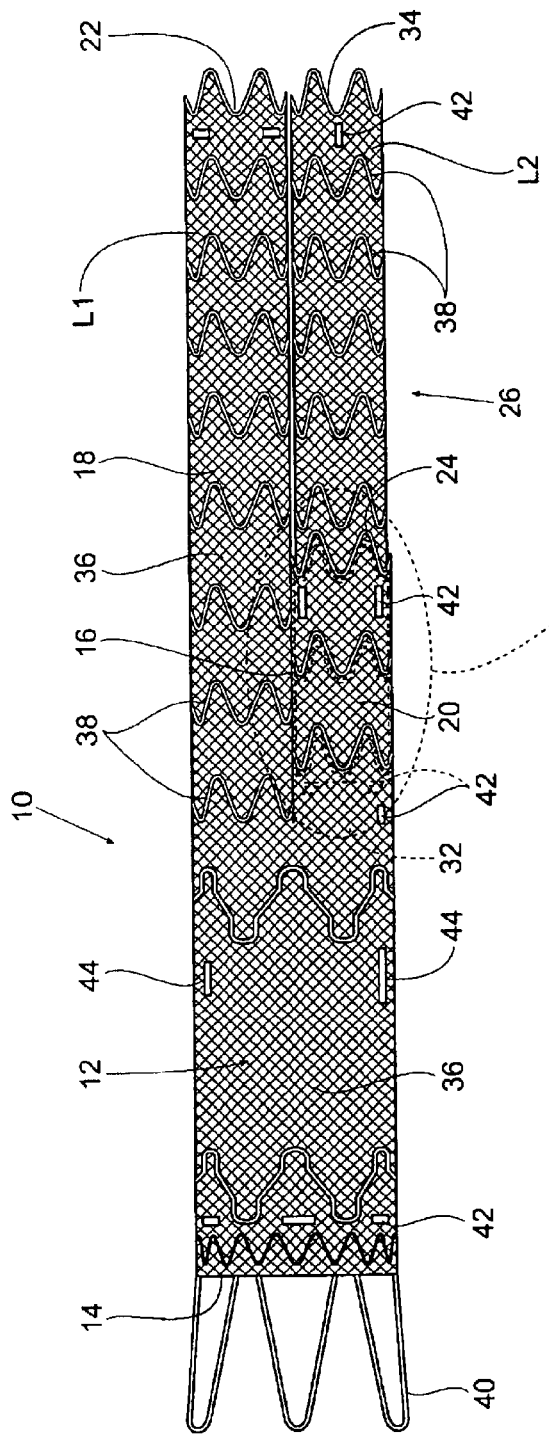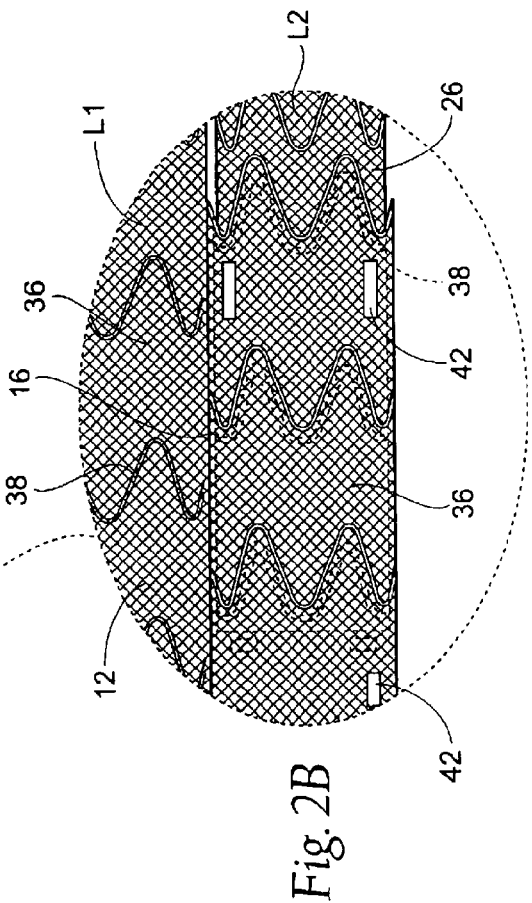
Fig. 2A
Fig. 2B

MULTI-LUMEN PROSTHESIS SYSTEMS AND METHODS

This application claims the benefit of U.S. Provisional Patent Application Ser. No. 60/489,011, filed Jul. 21, 2003, and entitled "Bifurcated Prosthesis Systems and Methods." This application is also a continuation-in-part of co-pending U.S. Patent Application Ser. No. 10/271,334, filed Oct. 15, 2002, entitled "Endovascular Aneurysm Repair System," which claims the benefit of U.S. Provisional Patent Application Ser. No. 60/333,937, filed Nov. 28, 2001.

BACKGROUND OF THE INVENTION

1. Field of the Invention

The invention relates generally to prostheses, and in particular, to prostheses used in the repair of diseased and/or damaged sections of a hollow body organ and/or a blood vessel.

2. Background of the Invention

The weakening of a vessel wall from damage or disease can lead to vessel dilatation and the formation of an aneurysm. Left untreated, an aneurysm can grow in size and may eventually rupture.

For example, aneurysms of the aorta primarily occur in abdominal region, usually in the infrarenal area between the renal arteries and the aortic bifurcation. Aneurysms can also occur in the thoracic region between the aortic arch and renal arteries. The rupture of an aortic aneurysm results in massive hemorrhaging and has a high rate of mortality.

Open surgical replacement of a diseased or damaged section of vessel can eliminate the risk of vessel rupture. In this procedure, the diseased or damaged section of vessel is removed and a prosthetic graft, made either in a straight of bifurcated configuration, is installed and then permanently attached and sealed to the ends of the native vessel by suture. The prosthetic grafts for these procedures are usually unsupported woven tubes and are typically made from polyester, ePTFE or other suitable materials. The grafts are longitudinally unsupported so they can accommodate changes in the morphology of the aneurysm and native vessel. However, these procedures require a large surgical incision and have a high rate of morbidity and mortality. In addition, many patients are unsuitable for this type of major surgery due to other co-morbidities.

Endovascular aneurysm repair has been introduced to overcome the problems associated with open surgical repair. The aneurysm is bridged with a vascular prosthesis, which is placed intraluminally. Typically these prosthetic grafts for aortic aneurysms are delivered collapsed on a catheter through the femoral artery. These grafts are usually designed with a fabric material attached to a metallic scaffolding (stent) structure, which expands or is expanded to contact the internal diameter of the vessel. Unlike open surgical aneurysm repair, intraluminally deployed grafts are not sutured to the native vessel, but rely on either barbs extending from the stent, which penetrate into the native vessel during deployment, or the radial expansion force of the stent itself is utilized to hold the graft in position. These graft attachment means do not provide the same level of attachment when compared to suture and can damage the native vessel upon deployment.

SUMMARY OF THE INVENTION

The invention provides apparatus and methods for repairing diseased and/or damaged sections of a hollow body organ and/or a blood vessel.

One aspect of the invention provides a prosthesis for a blood vessel or hollow body organ. The prosthesis comprises a trunk having an interior. An internal septum in the interior is sized and configured to define, within at least a portion of the trunk interior, a multi-lumen flow channel configuration. In one embodiment, the multi-lumen flow channel configuration includes a first interior lumen and a second interior lumen. At least one of the interior lumens is sized and configured to receive a lumen extension component to define an extended lumen.

Another aspect of the invention provides a method for deploying a prosthesis. The method introduces a prosthesis as above-described into a targeted site comprising a blood vessel or hollow body organ. The method locates the trunk of the prosthesis in contact with body tissue at the targeted site. The method can also fit the lumen extension to the trunk. In one embodiment, the method fastens the trunk to body tissue at the targeted site.

Other features and advantages of the invention shall be apparent based upon the accompanying description, drawings, and claims.

BRIEF DESCRIPTION OF THE DRAWINGS

The invention will be understood from the following detailed description of preferred embodiments, taken in conjunction with the accompanying drawings, wherein:

FIG. 2A is a side view of the multi-lumen prosthesis assembly shown in FIG. 1 in an assembled condition.

FIG. 2B is an enlarged view of the multi-lumen prosthesis assembly shown in FIG. 2A, showing the telescopic fitment within the interface region between the extension component and the second lumen of the main trunk.

DETAILED DESCRIPTION OF THE INVENTION

I. Multi-Lumen Prosthesis Assembly

Figure 1:
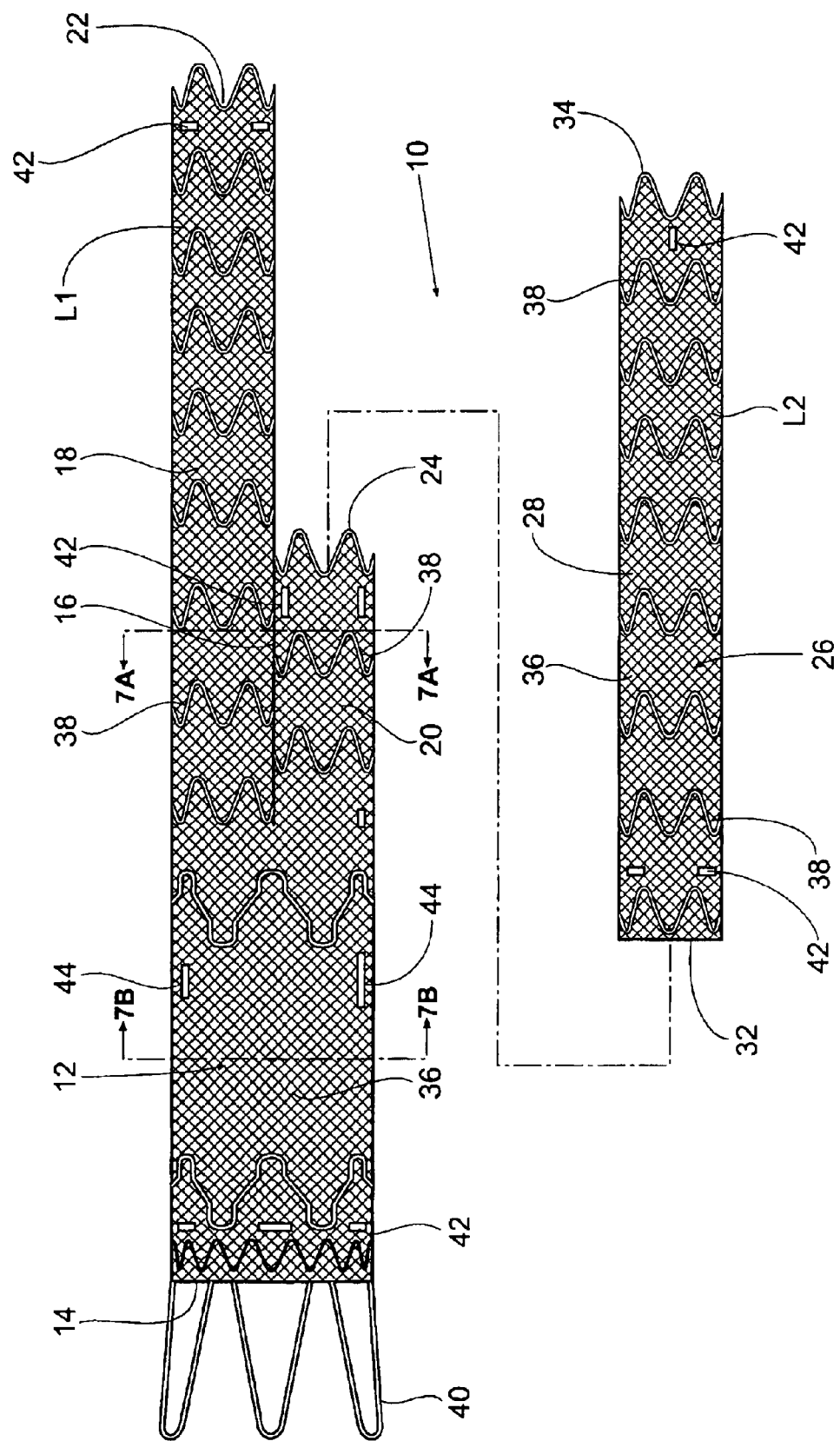
FIG. 1 is a side view of a multi-lumen prosthesis assembly that embodies features of the invention, the prosthesis assembly comprising two components prior to assembly.

FIG. 1 shows a multi-lumen prosthesis assembly 10 that embodies features of the invention. In the illustrated embodiment, the multi-lumen prosthesis assembly 10 comprises a trunk component 12 and at least one extension component 26.

The trunk component 12 is sized and configured to fit within a hollow body organ and/or a blood vessel. As described in this specification, the targeted site of deployment is within the aorta adjacent the renal arteries, as will be described in greater detail later. However, this targeted site of deployment is selected for purposes of illustrating the features of the assembly 10, and is not intended to be limiting.

The trunk component 12 includes an interior communicating with a proximal opening 14 for fluid flow into or from the prosthesis. The trunk component 12 includes a septum 16 within its interior. The length of the septum 16 within the prosthesis can vary. In the illustrated embodiment, the septum 16 does not extend along the entire length of the trunk component 12, but is spaced a distance from the proximal opening 14. In the illustrated arrangement, the septum 16 comprises a longitudinal seam. The seam can be formed, e.g., by sewing, heat bonding, or weaving opposing surfaces (i.e., the front and back) of the material 36 (which is typically a fabric) of the trunk component 12 together, thereby creating a septum or shared, common wall between two lumens 18 and 20 (see FIGS. 7A and 7B).

Figure 7A:
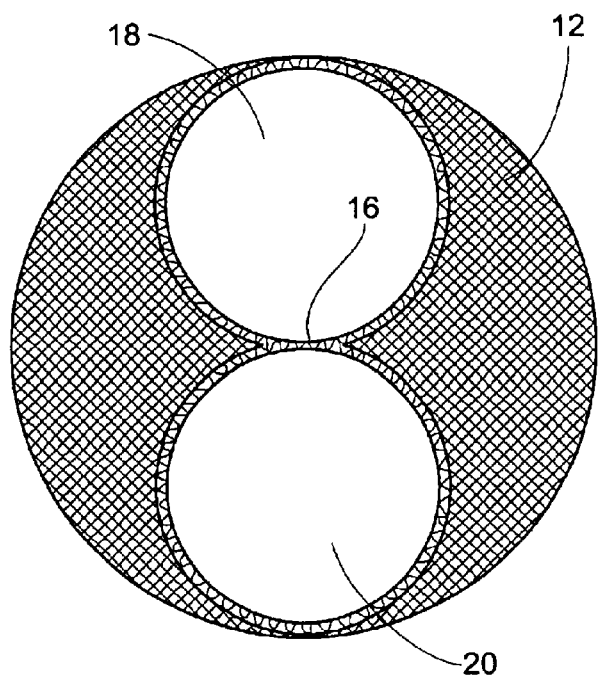
FIG. 7A is a section view of the distal end of the trunk component of the multi-lumen prosthesis assembly taken generally along line 7A—7A of FIG. 1.
Figure 7B:
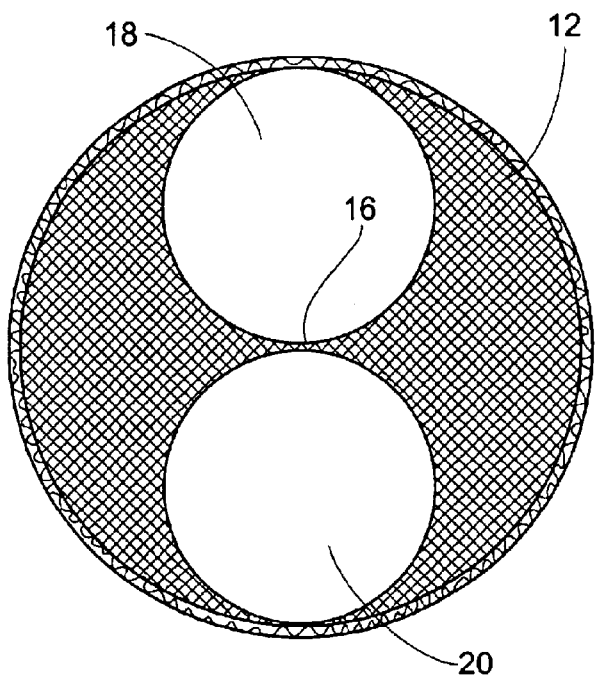
FIG. 7B is a section view of the proximal end of the trunk component of the multi-lumen prosthesis assembly taken generally along line 7B—7B of FIG. 1.

The septum 16 transforms at least a portion of the interior of the trunk component 12 into a multi-lumen flow channel configuration. In the illustrated embodiment, the multi-lumen flow channel configuration comprises dual first and second interior lumens 18 and 20. Due to the septum 16, the dual first and second interior lumens 18 and 20 of the multi-lumen flow channel configuration do not form branched or divergent legs (as FIGS. 7A and 7B show). The shared common wall (the septum 16) prevents divergence and maintains the lumens 18 and 20 in a non-divergent, generally parallel flow relationship (as FIGS. 7A and 7B show).

In the illustrated arrangement, the septum 16 runs generally along the mid-line of the trunk component 12, making the multi-lumen flow channel configuration within the trunk component 12 essentially symmetric. However, it should be appreciated that the septum 16 could form a non-symmetric multi-lumen flow channel configuration. It should also be appreciated that multiple septums can be present within the interior, transforming the interior of the trunk component 12 into a several flow lumens. The length of the septum can vary. In a representative embodiment, the septum is typically greater than 10 mm in length and not less than 5 mm in length.

In the illustrated embodiment, the second lumen 20 is truncated along at least a portion of the septum 16. As a result, the distal opening 22 of the first lumen 18 can be said to extend beyond the distal opening 24 of the second lumen 20. Still, the shared common wall (the septum 16) prevents divergence and maintains the lumens 18 and 20 in a non-divergent, generally parallel flow relationship.

The first lumen 18 defines a flow channel sized and configured to reach a targeted destination or source spaced a defined distance from the proximal opening 14, while the truncated second lumen 20 communicates with generally the same targeted destination as the proximal opening 14 of the trunk component 12 itself. Furthermore, the septum 16 is sized and configured to accommodate the coupling of a flow channel extension to the truncated second lumen 20, to likewise extend its reach to another targeted source or destination spaced from the distal opening 24, if desired.

In this arrangement (see FIG. 2A), the multi-lumen prosthesis assembly 10 includes a flow channel extension component 26. The extension component 26 includes a proximal end 32 that is sized and configured to be telescopically fitted within the truncated second lumen 20 of the trunk component 12. The distal end 34 of the extension component 26 is sized and configured to extend the reach of the truncated second lumen 20 to another targeted destination or source spaced a defined distance from the proximal opening 14. As a result, a portion of the extended second lumen 20 is joined to the first lumen 18 by the septum 16, and a portion of the extended second lumen 20 is not joined by the septum 16 to the first lumen 18.

The truncated second lumen 20 of the trunk component 12, which is joined by the septum 16 to the first lumen 18, provides an interface region or socket that, like the second lumen 18, is fully enclosed within the body of the trunk component 12 itself. The truncated second lumen 20 is therefore not prone to kinking or twisting or other kinds of movement independent of the trunk component 12. Passage of a guide wire through the second lumen 20 can occur unimpeded.

Being telescopically fitted within the interface region or socket and enclosed within the trunk component 12, the mechanical properties of the extension component 26 are supplemented by the structural support and integrity of the trunk component 12 itself, and vice versa. Coupled together, the trunk component 12 and the extension component 26 provide enhanced resistance to migration and/or separation of the extension component 26 from the trunk component 12. Seated within the enclosed interface region, the extension component 26 is peripherally sealed within the trunk component 12 to resist leaks or seepage of fluids around the extension component 26. The septum 16 can be tapered, curved, wavy, or otherwise non-linear to enhance the connection between the extension component and the trunk component 12.

Figure 3:
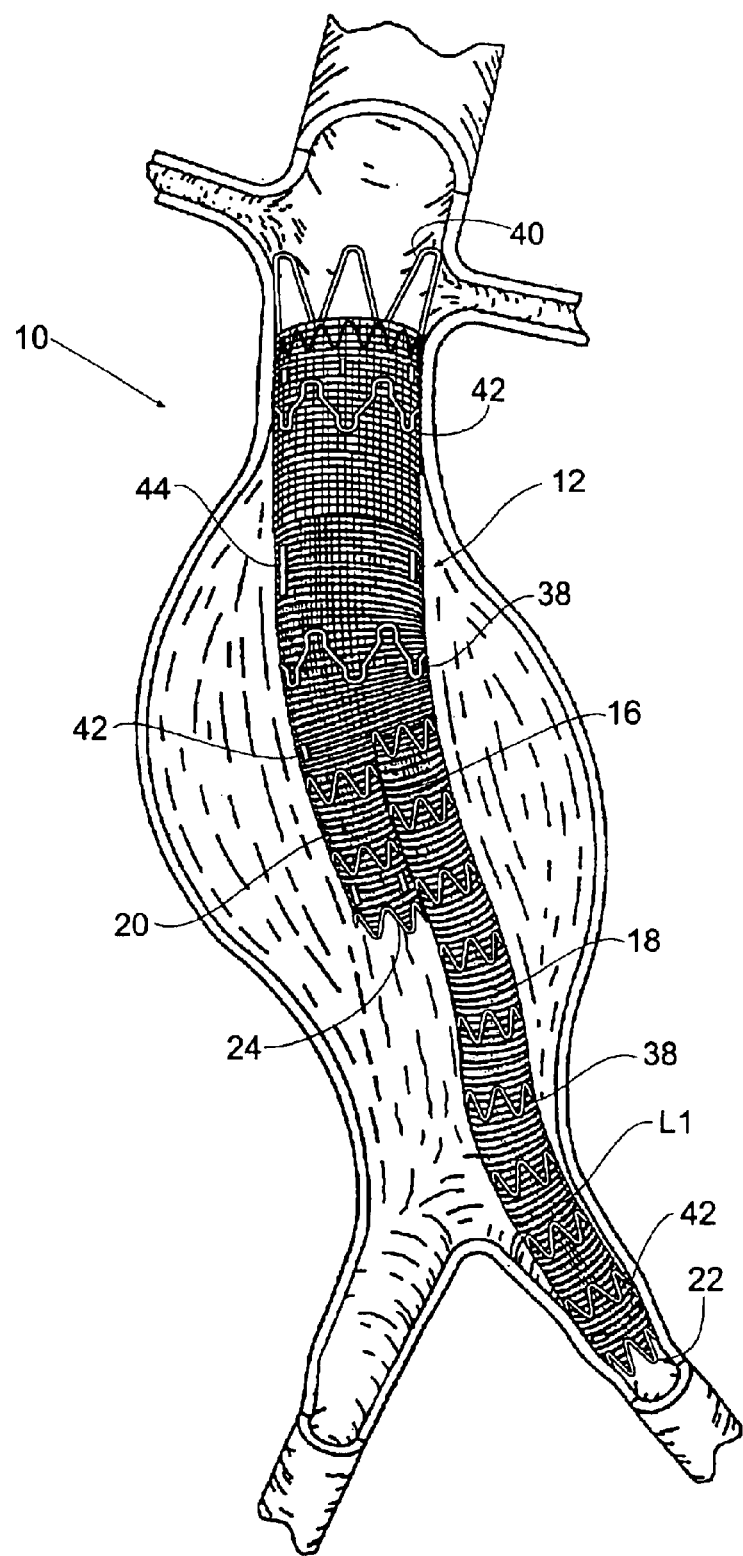
FIG. 3 is a perspective view of the first component of the multi-lumen prosthesis assembly shown in FIG. 1 positioned within an abdominal aortic aneurysm, with a main trunk of the first component being located within the aorta and a leg of the first component being located in an iliac.

In one illustrated use (see FIG. 3), the trunk component 12 can be deployed in the aorta in the region of the bifurcation of the first and second iliac. When properly deployed, the first lumen 18 can be sized to reach into the first iliac of the bifurcation, while the second lumen 20 remains in communication with the aorta. After the trunk component 12 is deployed (see FIG. 4), the extension component 26 can be fitted within the opening 24 of the second lumen 20, so that the distal end 34 of the second lumen 20 can reach into the second iliac of the bifurcation. In this arrangement, the first lumen 18 serves as a first leg L1 of the prosthesis, and the extension component 26 serves as a contralateral leg L2.

As described, both trunk and extension components 12 and 26 desirably utilize a prosthetic material 36 carrying individual self-expanding, zigzag type stent rings 38. The stent rings 38 need not be attached to one another throughout the prosthesis. However, it may be desirable in certain locations within the prosthesis structure to have attachments between the individual stent rings 38 to provide stability and/or additional radial support. As before stated, the septum 16 is formed by sewing, heat bonding, or weaving opposing surfaces (i.e., the front and back) of the prosthetic material 36 of the trunk component 12 together. In the region of the septum 16, the stent rings 38 extend from the septum 16 about the formed lumen, but do not enter or otherwise interrupt the septum 16 itself. The septum 16 is continuous and is formed separate from the supporting structure of stent rings 38.

The individual stent rings 38 allow for longitudinal prosthesis compliance while maintaining radial support of the prosthesis lumens. This technical features allows the prosthesis to more readily accommodate changes in vessel/aneurysm morphology.

The stent rings 38 can be made, e.g., from Nitinol® wire. Still, other materials, manufacturing methods and designs can be used. Each of the stent rings 38 is sewn onto prosthetic material 36. In certain locations it is desired to have the stent rings 38 attached to the outer diameter of the prosthetic material 36. Still, it is also contemplated that the stent rings 38 could be attached to the inner diameter of the prosthetic material 36.

In the illustrated embodiment, the prosthetic material 36 is woven polyester, and the attachment of the stent rings 38 is made with polyester suture. However, it is also contemplated that other attachment means could be utilized to secure the stent rings 38 to the prosthetic material 36. These means include bonding; capturing the stent rings 38 between two layers of prosthetic material 36; and incorporating the stent rings 38 directly into the woven prosthetic material 36.

The trunk component 12 may include a supra-renal stent 40 at its proximal end, which extends beyond the prosthetic material 36. When deployed within the aorta, this stent would extend above the level of the renal arteries. The supra-renal stent orients the prosthesis within the lumen and aids in maintaining the position of the prosthesis in the aorta without obstructing the normal blood flow into the renal arteries.

In the trunk component 12, the proximal end of the prosthesis (distal to the supra-renal stent 40) typically has one or more stent rings 38. The purpose of the stent rings 38 is to provide a seal between the vessel wall and the graft so that blood does not flow outside of the prosthesis and to help maintain the position of the prosthesis in the aorta. Typically, this region of the aorta (proximal neck of the aneurysm just below the renal arteries) is also where one or more fasteners may desirably be introduced by a fastener attachment assembly to anchor the prosthesis in place. Further details of the fastener attachment assembly can be found in U.S. patent application Ser. No. 10/307,226, filed Nov. 29, 2002, which is incorporated herein by reference. It is desirable that this region of the trunk component 12 be sized and configured for the receipt and retention of fasteners, e.g., the size and spacing of ring stent patterns to specially accommodate the placement of fasteners; and/or the use of woven fibers with an "X-pattern" or a "sinusoidal pattern" to specially accommodate placement of fasteners; and/or to fold over the prosthetic material to form multiple layers, to reinforce the prosthesis in the region where fasteners are placed; and/or the use of denser weave patters or stronger fibers from, e.g., Kevlarw material or Vectran™ material or metallic wire woven alone or interwoven with typical polyester fibers in the region were fasteners are placed. It may also be desirable to fluoroscopically indicate this region of the prosthesis with radiopaque markers 42 on the prosthetic material 36 or stent rings 38 to aid in positioning the fastening staples.

Additional stent rings 38 may be utilized throughout the main trunk of the first component 12. Desirably, a minimal number of stent rings 38 would be utilized within the trunk component 12. Typically, however, a stent ring 38 would be attached just proximal to the longitudinal seam 16 in the main trunk.

The longitudinal seam 16 in the main trunk can be created by methods such as sewing, heat bonding, or possibly weaving the front and the back of the prosthetic material 36 together. Typically the seam 16 would be located along the midline of the main trunk to create two equally sized lumens 18 and 20. However, the location of the seam 16 could be moved, if different sized lumens were desired.

The multiple lumens 18 and 20 in the trunk component 12 may typically be supported with stent rings 38 on the inside of the prosthetic material 36. Ideally, the stent rings 38 in one lumen 18 are staggered in position with the stent rings 38 in the other lumen 20, so that they do not overlap each other when the first component 12 is radially compressed prior to deployment. Typically, stent rings 38 would be attached to the outside of the first lumen 18 of the trunk component 12.

Rotational orientation of the trunk component 12 within the vessel lumen or hollow body organ is accomplished with additional radiopaque markers 44 attached to the prosthesis for visualization under fluoroscopy. Typically, these markers 44 may be attached to the prosthetic material 36. Still, the markers 44 may be attached to stent rings 38 instead of or in addition to the prosthetic material 36. The radiopaque markers 44 typically are in the form of marker bands, tight wound coils, or wire made from radiopaque materials such as platinum, platinum/iridium, or gold. The radiopaque markers 44 may be attached to the prosthetic material 36 or stent rings 38 to help fluoroscopically determine the location of all prosthesis openings and to indicate the insertion depth for the extension component 26 into the second lumen 20 of the trunk component 12. Desirably, two markers 44, one longer than the other, are attached on opposite sides of the main trunk of the first component 12 with the longer marker aligned on the side with the leg L1. The two markers 44 enable the user to determine the proper rotational orientation of the prosthesis in the delivery system so that, upon deployment, the second distal opening 20 is aligned with the contralateral iliac artery.

The extension component 26 has stent rings 38 attached to the outside of prosthetic material 36 along its entire length, with some spacing between the stent rings 38. However, as in the trunk component 12, it is contemplated that the stent rings 38 could also be placed on the inside of the prosthetic material 36. Furthermore, as previously discussed, the stent rings 38 need not be attached to one another throughout the prosthesis. However, it may be desirable in certain locations within the prosthesis structure to have attachments between the individual stent rings 38 to provide stability and/or additional radial support. The addition of the stent rings 38 to the extension component 26 aids in the deployment of the extension component 26 and allows for longitudinal compliance while maintaining radial support of the lumen within the extension component 26. Typically, radiopaque markers 42 are used on each end of the prosthesis to aid in the visualization of the placement of the extension component 26 within the lumen of the second distal opening 24 of the first component 12.

As shown in FIGS. 2A and 2B, the stent rings 38 in the extension component 26 can be sized, configured, and arranged to engage the stent rings 38 in the second lumen 20 of the main trunk 12. This engagement prevents the extension component 26 from moving or migrating longitudinally in relating to the second lumen 20 after the extension component 26 has been deployed.

II. Use of the Multilumen Prosthesis Assembly

Figure 5:
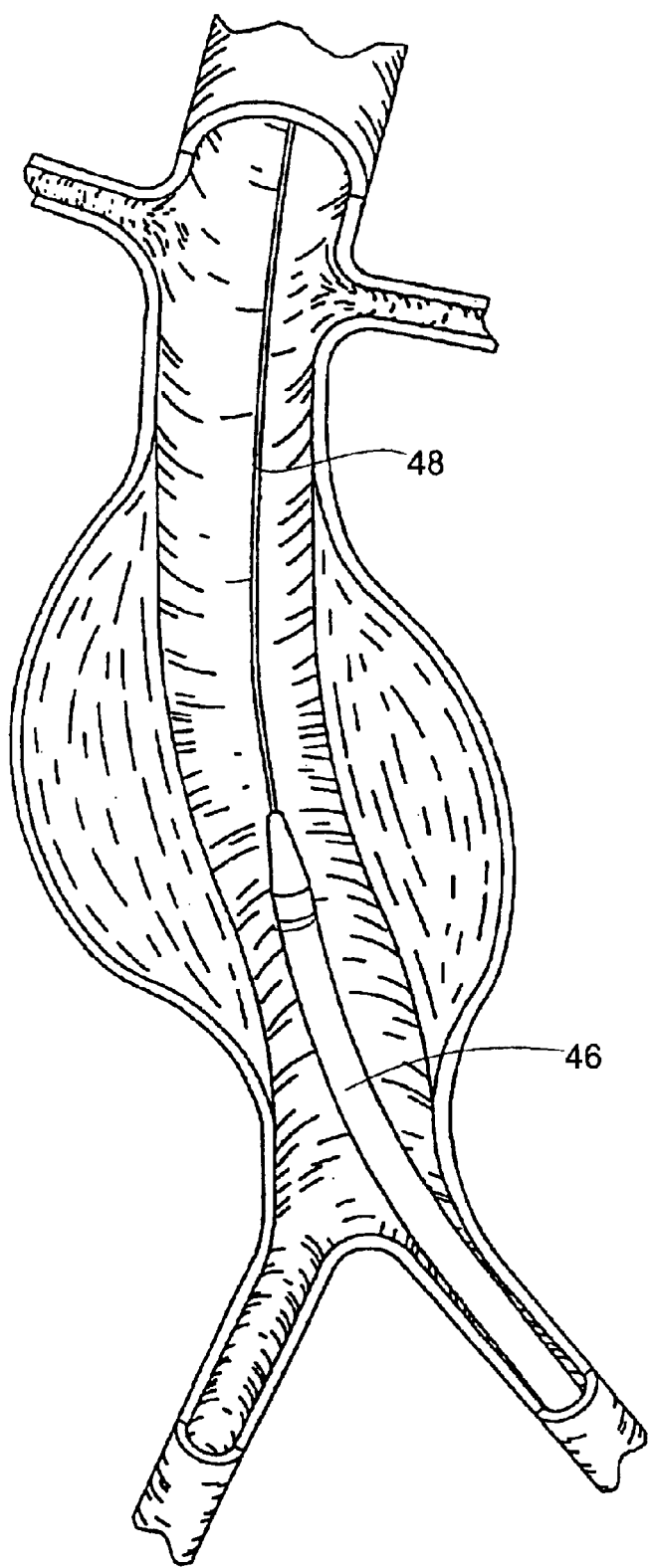
FIG. 5 is a perspective view of an endovascular graft delivery catheter carrying the first component of the multi-lumen prosthesis assembly in a radially compressed condition into a desired location within an abdominal aortic aneurysm, the first component, upon deployment by the catheter, radially expanding to the condition shown in FIG. 3.

During use (see FIG. 5), a first catheter 46 is navigated over a guide wire 48 through an iliac to the desired location within the aorta near the renal arteries. The catheter 46 carries the trunk component 12 of the multi-lumen prosthesis system 10 in a radially reduced configuration. At the targeted site, the catheter 46 releases the trunk component 12, which expands radially into the position shown in FIG. 3.

Figure 4:
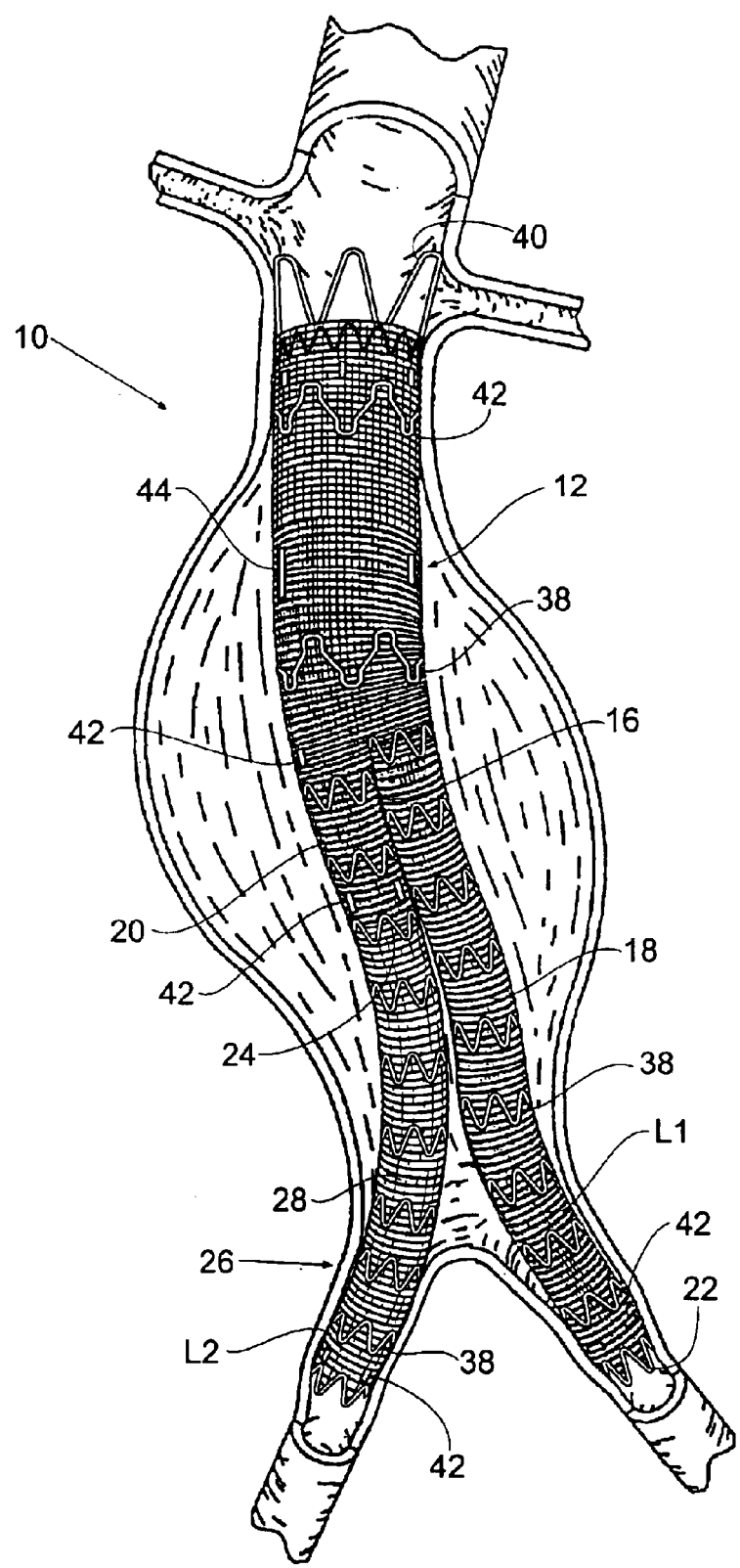
FIG. 4 is a perspective view of the first and second components of the multi-lumen prosthesis assembly after their assembly within an abdominal aortic aneurysm, showing the first component being located within the aorta, with one leg in an iliac, and the second component being located telescopically within the first component with a leg extending into a contralateral iliac.
Figure 6:
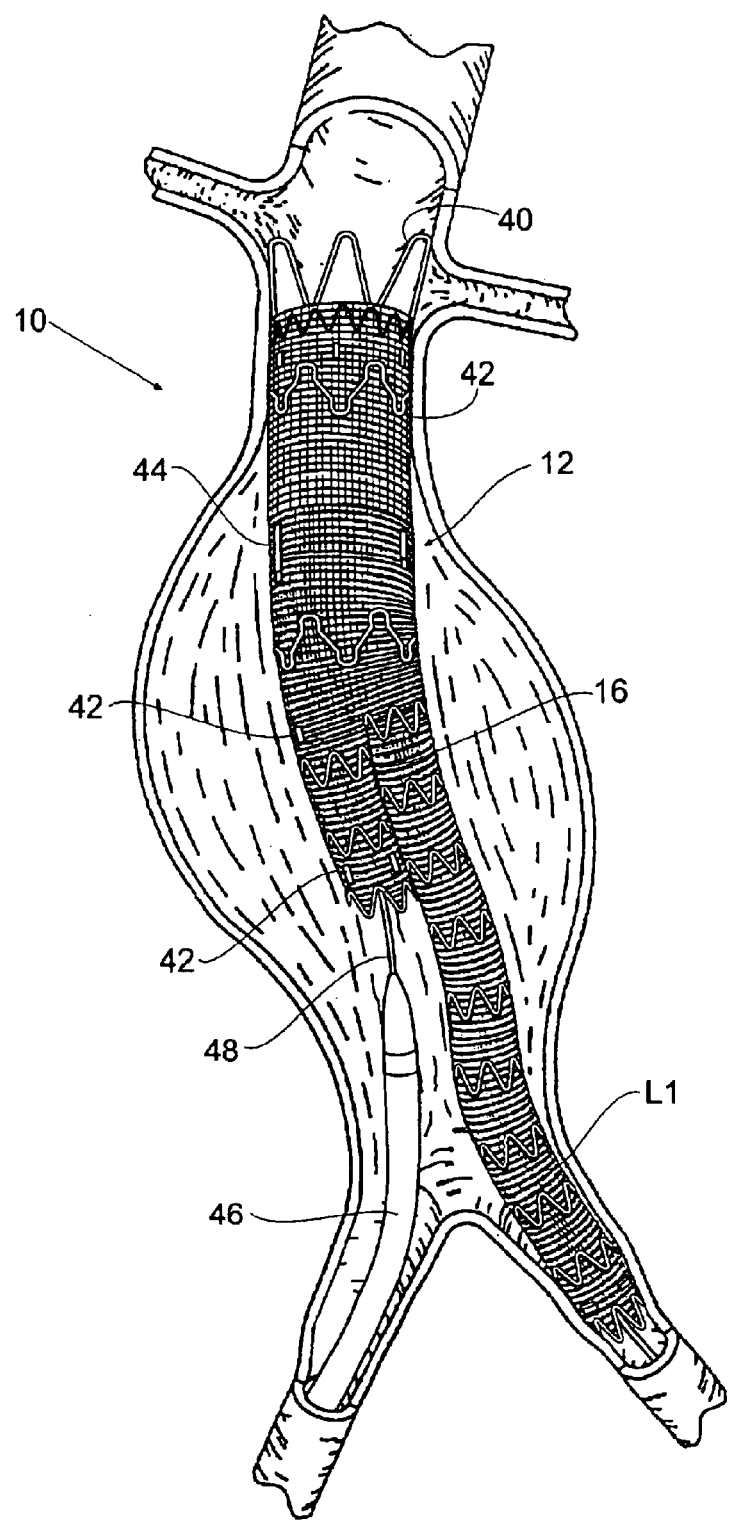
FIG. 6 is a perspective view of an endovascular graft delivery catheter carrying the second component of the multi-lumen prosthesis assembly in a radially compressed condition into association with the previously deployed first component, the second component, upon deployment by the catheter, radially expanding to the condition shown in FIG. 4.

As FIG. 6 shows, the extension component 26 is carried in a radially compressed condition by another over-the-wire catheter 50 coming from the contralateral iliac. The catheter 50 deploys the extension component 26, such that the proximal end of the extension component 26 is telescopically received within the second lumen 20 of the trunk component 12 and the distal end extends into the contralateral iliac, as FIG. 4 shows. Only when the extension component 26 is telescopically received within the second lumen 20 of the trunk component 12, a bifurcated prosthesis is formed with divergent legs.

The preferred embodiments of the invention are described above in detail for the purpose of setting forth a complete disclosure and for the sake of explanation and clarity. Those skilled in the art will envision other modifications within the scope and sprit of the present disclosure.

The above described embodiments of this invention are merely descriptive of its principles and are not to be limited. The scope of this invention instead shall be determined from the scope of the following claims, including their equivalents.

We claim:

1. A prosthesis assembly for a blood vessel or hollow body organ comprising,
    a trunk including a prosthetic material having an interior including a seam joining opposing surfaces of the prosthetic material together to form an internal septum sized and configured to define, within at least a portion of the trunk interior, a multi-lumen flow channel configuration comprising a trunk lumen, at least a first interior lumen and a truncated second interior lumen that is shorter than the first interior lumen, wherein the first interior lumen and the truncate second interior lumen extend along the internal septum, at least two stent structures carried in a spaced apart relationship along each of the first interior lumen and the truncated second interior lumen to support the respective interior lumen, the septum being formed separate from the stent structures, the stent structures in one of the interior lumens being staggered in position with respect to the stent structures in the other interior lumen such that the stent structures in the first interior lumen do not overlap or align with the stent structures in the truncated second interior lumen, and
    a lumen extension component sized and configured to be fitted within at least one of the first and truncated second interior lumens to define an extension of the at least one interior lumen.

2. An assembly according to claim 1
wherein the first interior lumen includes a region that is joined by the septum to the truncated second interior lumen and another region that is not joined by the septum to the truncated second interior lumen and that extends beyond the truncated second interior lumen.

3. An assembly according to claim 1
wherein a region of the trunk is sized and configured to receive a fastening element to secure the trunk to body tissue.

4. An assembly according to claim 1
wherein the prosthetic material includes a fabric.

5. An assembly according to claim 1
wherein the lumen extension component includes a prosthetic material.

6. An assembly according to claim 1
wherein the lumen extension component includes scaffolding.

7. An assembly according to claim 6
wherein the scaffolding includes at least one stent structure.

8. An assembly according to claim 6
wherein the scaffolding includes a self-expanding stent ring.

9. An assembly according to claim 6
wherein the scaffolding includes spaced apart stent structures.

10. An assembly according to claim 9
wherein the spaced apart stent structures include first and second adjacent stent structures that are not mutually attached one to the other.

11. An assembly according to claim 9
wherein the spaced apart stent structures include first and second adjacent stent structures that are mutually attached one to the other.

12. An assembly according to claim 1
wherein the trunk extends along an axis,
wherein the septum comprises a seam formed along the axis of the trunk.

13. An assembly according to claim 1
wherein the seam is formed by weaving.

14. An assembly according to claim 1
wherein at least one of the stent structures comprises a stent ring.

15. An assembly according to claim 1
wherein all of the stent structures comprise stent rings.

16. An assembly according to claim 1
wherein the spaced apart stent structures in at least one of the interior lumens include first and second adjacent stent structures that are not mutually attached one to the other.

17. An assembly according to claim 1
wherein the spaced apart stent structures in at least one of the interior lumens includes first and second adjacent stent structures that are mutually attached one to the other.

18. A method for deploying a prosthesis comprising the steps of
    introducing a prosthesis assembly as defined in claim 1 into a targeted site comprising a blood vessel or hollow body organ,
    locating the trunk of the prosthesis assembly in contact with body tissue at the targeted site, and
    fitting the lumen extension of the prosthesis assembly to the trunk.

19. A method according to claim 18
further including the step of fastening the trunk of the prosthesis assembly to body tissue at the targeted site.

* * * * *

UNITED STATES PATENT AND TRADEMARK OFFICE
CERTIFICATE OF CORRECTION

PATENT NO. : 6,929,661 B2
DATED : August 16, 2005
INVENTOR(S) : Lee Bolduc and Andrew L. Chiang It is certified that error appears in the above-identified patent and that said Letters Patent is hereby corrected as shown below:

<u>Column 8,</u>
Line 42, after "lumens" delete "includes" and substitute -- include --.

Signed and Sealed this

Thirty-first Day of January, 2006

JON W. DUDAS
*Director of the United States Patent and Trademark Office*